(12) United States Patent
Adams et al.

(10) Patent No.: US 8,521,555 B2
(45) Date of Patent: Aug. 27, 2013

(54) SYSTEM AND METHOD USING A PREDICTIVE MODEL FOR NURSE INTERVENTION PROGRAM DECISIONS

(75) Inventors: Jonathan Kaleb Adams, Middletown, CT (US); Ryan A. Gawel, Bristol, CT (US); Joseph D. Pagano, Wallingford, CT (US)

(73) Assignee: Hartford Fire Insurance Company, Hartford, CT (US)

( * ) Notice: Subject to any disclaimer, the term of this patent is extended or adjusted under 35 U.S.C. 154(b) by 385 days.

(21) Appl. No.: 12/634,046

(22) Filed: Dec. 9, 2009

(65) Prior Publication Data

US 2011/0137672 A1 Jun. 9, 2011

(51) Int. Cl.
*G06Q 10/00* (2012.01)
*G06Q 50/00* (2012.01)
*G06Q 40/00* (2012.01)

(52) U.S. Cl.
USPC ........................................ 705/2; 705/3; 705/4

(58) Field of Classification Search
USPC ........................................................ 705/2–4
See application file for complete search history.

(56) References Cited

U.S. PATENT DOCUMENTS

| 5,277,188 | A | * | 1/1994 | Selker | 600/508 |
| 5,471,382 | A | * | 11/1995 | Tallman et al. | 600/300 |
| 5,764,923 | A | * | 6/1998 | Tallman et al. | 705/3 |
| 6,383,135 | B1 | * | 5/2002 | Chikovani et al. | 600/300 |
| 6,767,325 | B2 | * | 7/2004 | Iliff | 600/300 |
| 6,786,406 | B1 | * | 9/2004 | Maningas | 235/385 |
| 6,849,045 | B2 | * | 2/2005 | Iliff | 600/300 |
| 7,300,402 | B2 | * | 11/2007 | Iliff | 600/300 |
| 7,363,240 | B1 | | 4/2008 | Armentano et al. | |
| 7,925,559 | B2 | * | 4/2011 | Scully | 705/35 |
| 2002/0069089 | A1 | * | 6/2002 | Larkin et al. | 705/4 |
| 2002/0138306 | A1 | * | 9/2002 | Sabovich | 705/3 |
| 2009/0254379 | A1 | * | 10/2009 | Adams et al. | 705/4 |

FOREIGN PATENT DOCUMENTS

WO    WO 0113295 A1 * 2/2001

OTHER PUBLICATIONS

Nyce, Charles, "Predictive Analytics", White Paper, American Institute for CPCU / Insurance Institute of America, 2007.*

* cited by examiner

*Primary Examiner* — Michael Fuelling
(74) *Attorney, Agent, or Firm* — Howard IP Law Group, PC (57) ABSTRACT

According to some embodiments, historical claim data may be stored in a computer storage unit. The historical claim data may be used to train and verify a predictive model, the predictive model being associated with an evaluation of claim transactions to determine whether to refer each claim transactions to a nurse intervention program. Data for current claim transactions may be processed, and the trained and verified predictive model may be applied to the data for the current claim transactions to generate a respective output for each of the current claim transactions. Some of the current claim transactions may be selectively routed to a case management center associated with the nurse intervention program based on the outputs generated by the predictive model.

14 Claims, 11 Drawing Sheets

SYSTEM AND METHOD USING A PREDICTIVE MODEL FOR NURSE INTERVENTION PROGRAM DECISIONS

FIELD

The present invention relates to computer systems and more particularly to computer systems that apply predictive models in connection with nurse intervention program decisions.

BACKGROUND

A nurse intervention program may be used to improve the health care services provided to an injured worker. Consider, for example, a worker who submits a workers compensation claim as a result of an injury he or she received while at work. In such a situation, an insurer might arrange for a nurse to visit and provide additional health care to the worker while he or she recovers at home. Note that the improved care could result in the worker returning to his or job sooner (as compared to a worker with a similar injury who did not receive additional health care). As a result, the insurer can also benefit from providing improved health care (e.g., because the worker returned to work sooner and thus a total amount of benefits paid by the insurer might be reduced). Determining when it is appropriate to utilize a nurse intervention program, however, can be a difficult and time consuming task. For example, the decision might depend on a nature of the injury as well as details about the particular claimant. Moreover, an insurer might handle claims associated with many different accounts, and each account might have different rules and benefits that need to be considered when determining whether or not a nurse intervention program is appropriate for a particular claim.

Although some systems have attempted to apply simple rules to help determine whether or not a nurse intervention program is appropriate for a particular claim, such approaches may not effectively identify which patients and/or injuries may benefit most from these services.

The present inventors have recognized the utility of a predictive model for determining that certain insurance claims should be identified and referred for a nurse intervention program. Moreover, the use of the predictive model can be significantly enhanced by expanding the types of information used to train the predictive model and included in current claim transaction data to which the predictive model is applied, as well as by considering account-specific information associated with a particular insurance claim.

SUMMARY

A computer system is disclosed which includes a data storage module to receive, store and provide access to historical claim transactions and to current claim transactions. The computer system further includes a predictive model component that is coupled to the data storage module and determines whether to identify a given one of the current claim transactions for referral to a nurse intervention program.

The computer system also includes a computer processor that executes programmed instructions and stores and retrieves the data related to current claim transactions. Further included in the computer system is a program memory, coupled to the computer processor, and which stores program instruction steps for execution by the computer processor.

A model training component is also included in the computer system. The model training component is coupled to the computer processor and trains the predictive model component based on the data related to the historical claim transactions in accordance with program instructions stored in the program memory and executed by the computer processor. As a consequence, a trained predictive model component is provided.

Still further included in the computer system is an output device. The output device is coupled to the computer processor and outputs an output indicative of whether the current claim transaction in question should be referred to a nurse intervention program. The computer processor generates the output in accordance with program instructions in the program memory and executed by the computer processor. The output is generated in response to application of data for the current claim transaction in question to the trained predictive model component. The computer system further includes a routing module which directs workflow based on the output from the output device.

The present inventors have observed that effective indicators in an insurance claim file that a claim may be beneficially referred to a nurse intervention program. By incorporating this data, or information extracted therefrom, in historical data used to train a predictive model, and in current transaction information applied to the predictive model, the performance of the predictive model may be enhanced, and the ability of the model to recommend nurse intervention may be improved. As a result, improved decisions associated with a nurse intervention program may be provided.

With these and other advantages and features of the invention that will become hereinafter apparent, the invention may be more clearly understood by reference to the following detailed description of the invention, the appended claims, and the drawings attached hereto.

DETAILED DESCRIPTION

In general, and for the purposes of introducing concepts of embodiments of the present invention, a computer system incorporates a "predictive model." As used herein, the phrase "predictive model" might refer to, for example, any of a class of algorithms that are used to understand relative factors contributing to an outcome, estimate unknown outcomes, discover trends, and/or make other estimations based on a data set of factors collected across prior trials. Note that a predictive model might refer to, but is not limited to, methods such as ordinary least squares regression, logistic regression, decision trees, neural networks, generalized linear models, and/or Bayesian models. The predictive model is trained with historical claim transaction data, and is applied to current claim transactions to determine whether the current claim transactions should be referred to a nurse intervention program. Both the historical claim transaction data and data representing the current claim transactions might include, according to some embodiments, indeterminate data or information extracted therefrom. For example, such data/information may come from narrative and/or medical text notes associated with a claim file.

Figure 1:
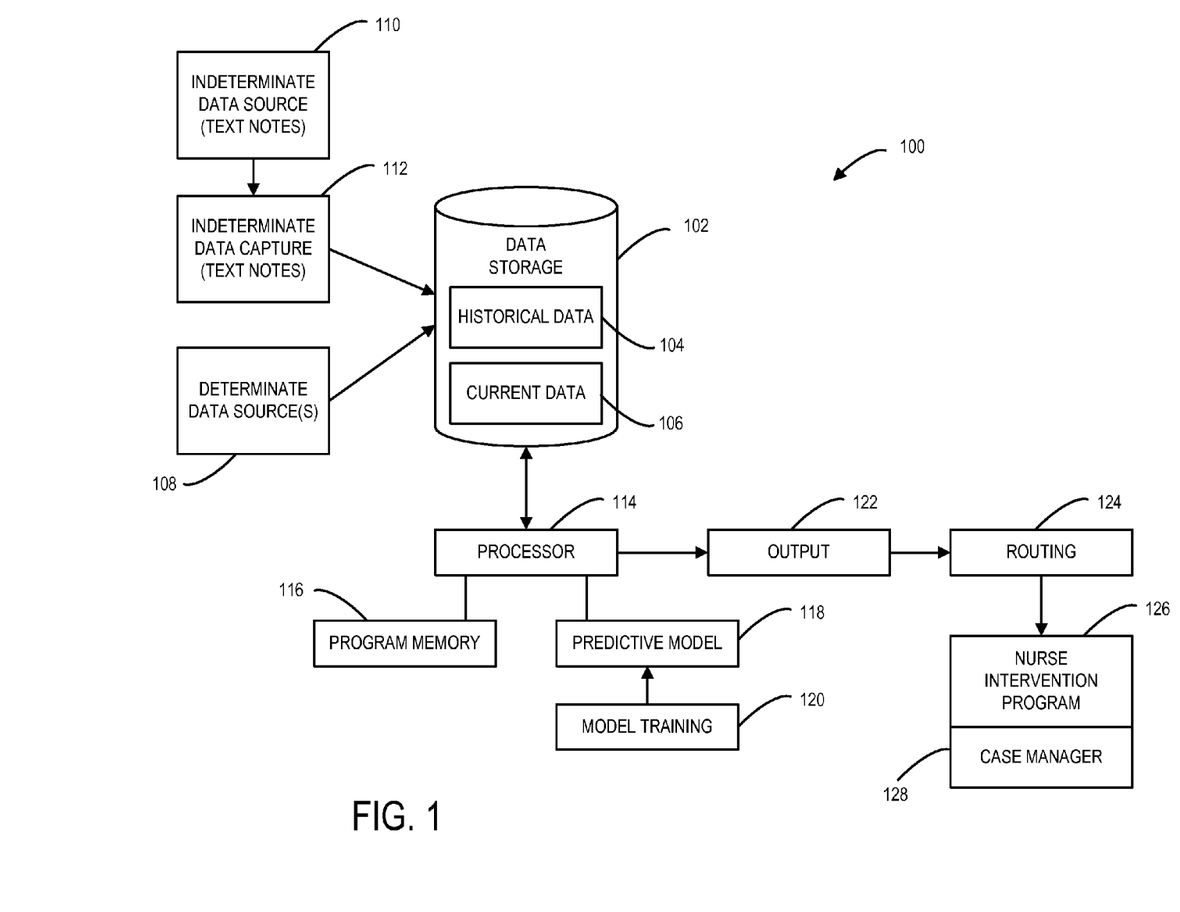
FIG. 1 is a partially functional block diagram that illustrates aspects of a computer system provided in accordance with some embodiments of the invention.

Features of some embodiments of the present invention will now be described by first referring to FIG. 1. FIG. 1 is a partially functional block diagram that illustrates aspects of a computer system 100 provided in accordance with some embodiments of the invention. For present purposes it will be assumed that the computer system 100 is operated by an insurance company (not separately shown) for the purpose of referring certain claims to a nurse intervention program when appropriate. The claims may be from one or more different lines of insurance, such as worker's compensation, property and casualty, etc.

The computer system 100 includes a data storage module 102. In terms of its hardware the data storage module 102 may be conventional, and may be composed, for example, by one or more magnetic hard disk drives. A function performed by the data storage module 102 in the computer system 100 is to receive, store and provide access to both historical claim transaction data (reference numeral 104) and current claim transaction data (reference numeral 106). As described in more detail below, the historical claim transaction data 104 is employed to train a predictive model to provide an output that indicates whether a claim should be referred to a nurse intervention program, and the current claim transaction data 106 is thereafter analyzed by the predictive model. Moreover, as time goes by, and results become known from providing nurse interventions for current claim transactions, at least some of the current claim transactions may be used to perform further training of the predictive model. Consequently, the predictive model may thereby adapt itself to changing patterns of claims.

Either the historical claim transaction data 104 or the current claim transaction data 106 might include, according to some embodiments, determinate and indeterminate data. As used herein and in the appended claims, "determinate data" refers to verifiable facts such as the date of birth, age or name of a claimant or name of another individual or of a business or other entity; a type of injury; a medical diagnosis; a date of loss, or date of report of claim, or policy date or other date; a time of day; a day of the week; a vehicle identification number, a geographic location; and a policy number.

As used herein and in the appended claims, "indeterminate data" refers to data or other information that is not in a predetermined format and/or location in a data record or data form. Examples of indeterminate data include narrative speech or text, information in descriptive notes fields and signal characteristics in audible voice data files. Indeterminate data extracted from medical notes might be associated with, for example, a prior injury, alcohol related co-morbidity information, drug related co-morbidity information, tobacco related co-morbidity information, arthritis related co-morbidity information, diabetes related co-morbidity information, and/or obesity related co-morbidity information.

The determinate data may come from one or more determinate data sources 108 that are included in the computer system 100 and are coupled to the data storage module 102. The determinate data may include "hard" data like the claimant's name, date of birth, social security number, policy number, address; the date of loss; the date the claim was reported, etc. One possible source of the determinate data may be the insurance company's policy database (not separately indicated). Another possible source of determinate data may be from data entry by the insurance company's claims intake administrative personnel.

The indeterminate data may originate from one or more indeterminate data sources 110, and may be extracted from raw files or the like by one or more indeterminate data capture modules 112. Both the indeterminate data source(s) 110 and the indeterminate data capture module(s) 112 may be included in the computer system 100 and coupled directly or indirectly to the data storage module 102. Examples of the indeterminate data source(s) 110 may include data storage facilities for document images, for text files (e.g., claim handlers' notes) and digitized recorded voice files (e.g., claimants' oral statements, witness interviews, claim handlers' oral notes, etc.). Examples of the indeterminate data capture module(s) 112 may include one or more optical character readers, a speech recognition device (i.e., speech-to-text conversion), a computer or computers programmed to perform natural language processing, a computer or computers programmed to identify and extract information from narrative text files, a computer or computers programmed to detect key words in text files, and a computer or computers programmed to detect indeterminate data regarding an individual. For example, claim handlers' opinions may be extracted from their narrative text file notes.

The computer system 100 also may include a computer processor 114. The computer processor 114 may include one or more conventional microprocessors and may operate to execute programmed instructions to provide functionality as described herein. Among other functions, the computer processor 114 may store and retrieve historical claim transaction data 104 and current claim transaction data 106 in and from the data storage module 102. Thus the computer processor 114 may be coupled to the data storage module 102.

The computer system 100 may further include a program memory 116 that is coupled to the computer processor 114. The program memory 116 may include one or more fixed storage devices, such as one or more hard disk drives, and one or more volatile storage devices, such as RAM (random access memory). The program memory 116 may be at least partially integrated with the data storage module 102. The program memory 116 may store one or more application programs, an operating system, device drivers, etc., all of which may contain program instruction steps for execution by the computer processor 114.

The computer system 100 further includes a predictive model component 118. In certain practical embodiments of the computer system 100, the predictive model component 118 may effectively be implemented via the computer processor 114, one or more application programs stored in the program memory 116, and data stored as a result of training operations based on the historical claim transaction data 104 (and possibly also data resulting from training with current claims that have benefited from nurse interventions). In some embodiments, data arising from model training may be stored in the data storage module 102, or in a separate data store (not separately shown). A function of the predictive model component 118 may be to identify current claim transactions that should be referred to a nurse intervention program. The predictive model component may be directly or indirectly coupled to the data storage module 102.

The predictive model component 118 may operate generally in accordance with conventional principles for predictive models, except, as noted herein, for at least some of the types of data to which the predictive model component is applied. Those who are skilled in the art are generally familiar with programming of predictive models. It is within the abilities of those who are skilled in the art, if guided by the teachings of this disclosure, to program a predictive model to operate as described herein.

Still further, the computer system 100 includes a model training component 120. The model training component 120 may be coupled to the computer processor 114 (directly or indirectly) and may have the function of training the predictive model component 118 based on the historical claim transaction data 104. (As will be understood from previous discussion, the model training component 120 may further train the predictive model component 118 as further relevant claim transaction data becomes available.) The model training component 120 may be embodied at least in part by the computer processor 114 and one or more application programs stored in the program memory 116. Thus the training of the predictive model component 118 by the model training component 120 may occur in accordance with program instructions stored in the program memory 116 and executed by the computer processor 114.

In addition, the computer system 100 may include an output device 122. The output device 122 may be coupled to the computer processor 114. A function of the output device 122 may be to provide an output that is indicative of whether (as determined by the trained predictive model component 118) a particular one of the current claim transactions should be referred to a nurse intervention program. The output may be generated by the computer processor 114 in accordance with program instructions stored in the program memory 116 and executed by the computer processor 114. More specifically, the output may be generated by the computer processor 114 in response to applying the data for the current claim transaction to the trained predictive model component 118. The output may, for example, be a true/false flag or a number within a predetermined range of numbers. In some embodiments, the output device may be implemented by a suitable program or program module executed by the computer processor 114 in response to operation of the predictive model component 118.

Still further, the computer system 100 may include a routing module 124. The routing module 124 may be implemented in some embodiments by a software module executed by the computer processor 114. The routing module 124 may have the function of directing workflow based on the output from the output device. Thus the routing module 124 may be coupled, at least functionally, to the output device 122. In some embodiments, for example, the routing module may direct workflow by referring, to a nurse intervention program 126, current claim transactions analyzed by the predictive model component 118 and found to be questionable. In particular, the questionable current claim transactions may be referred to case manager 128 who is associated with the nurse intervention program 126. The nurse intervention program 126 may be a part of the insurance company that operates the computer system 100, and the case manager 128 might be an employee of the insurance company.

Figure 2:
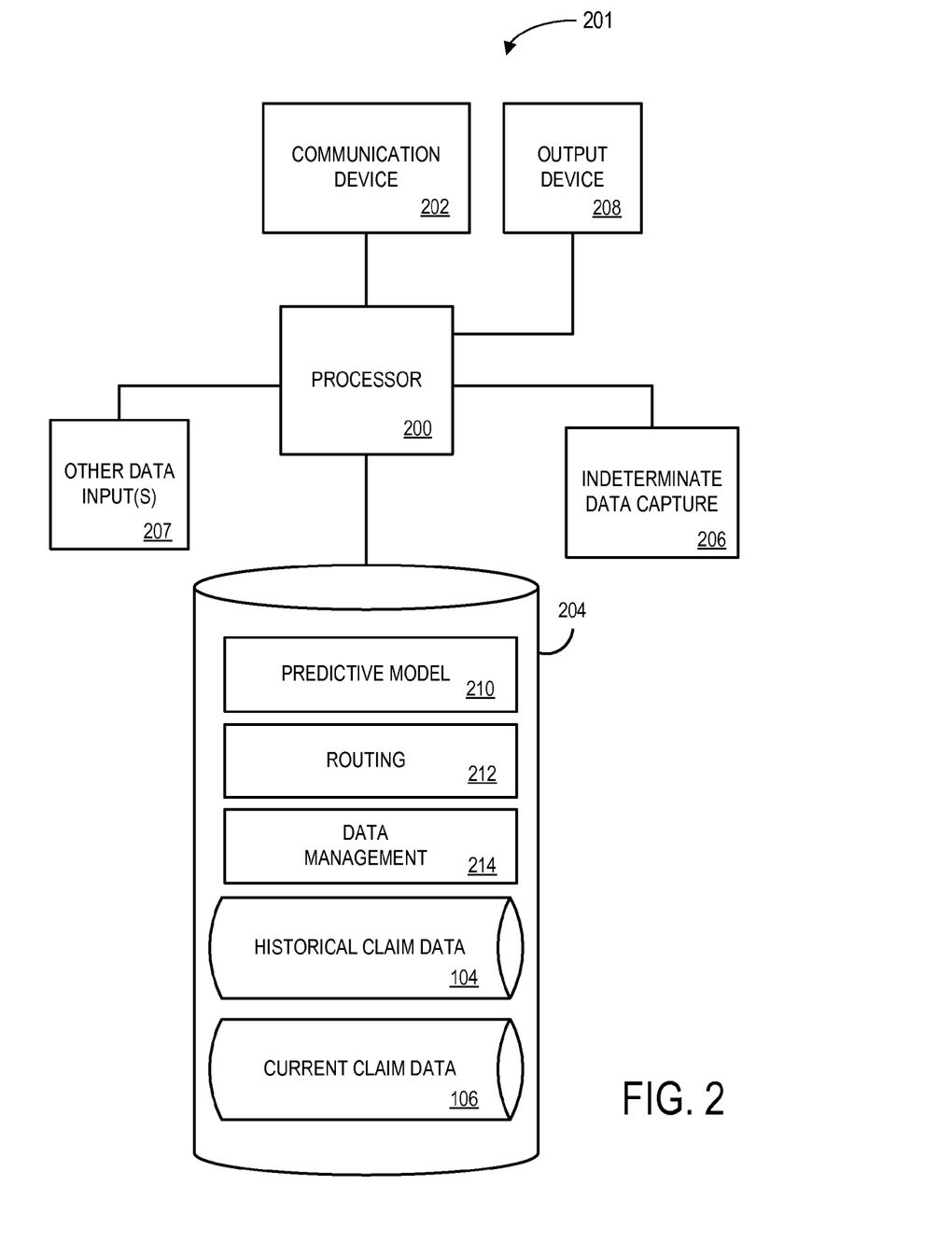
FIG. 2 is a block diagram that illustrates a computer that may form all or part of the system of FIG. 1.

FIG. 2 is a block diagram that illustrates a computer 201 that may form all or part of the system 100 of FIG. 1. As depicted, the computer 201 includes a computer processor 200 operatively coupled to a communication device 202, a storage device 204, an indeterminate data capture device 206, one or more other input devices 207 and an output device 208. Communication device 202 may be used to facilitate communication with, for example, other devices (such as personal computers—not shown in FIG. 2—assigned to individual employees of the insurance company). The indeterminate data capture device 206 may include any one or more of the devices referred to above in connection with block 112 in FIG. 1 and may have the functions ascribed above to those devices. The other input device(s) 207 may comprise, for example, a keyboard, a keypad, a mouse or other pointing device, a microphone, knob or a switch, an infra-red (IR) port, a docking station, and/or a touch screen. The other input device(s) 207 may be used, for example, to enter information. Output device 208 may comprise, for example, a display (e.g., a display screen) a speaker, and/or a printer.

Storage device 204 may comprise any appropriate information storage device, including combinations of magnetic storage devices (e.g., magnetic tape and hard disk drives), optical storage devices, and/or semiconductor memory devices such as Random Access Memory (RAM) devices and Read Only Memory (ROM) devices.

Storage device 204 stores one or more programs or portions of programs (at least some of which being indicated by blocks 210-214) for controlling processor 200. Processor 200 performs instructions of the programs, and thereby operates in accordance with the present invention. In some embodiments, the programs may include a program or program module 210 that acts as a predictive model for determining whether to refer current claim transactions to a nurse intervention program. The training function for the predictive model 210 is not indicated separately in FIG. 2 from the predictive model itself.

Another program or program module stored on the storage device 204 is indicated at block 212 and is operative to allow the computer 201 to route or refer current claim transactions to insurance company employees as appropriate based on the results obtained by applying the predictive model 210 to the data which represents the current claim transactions.

Still another program or program module stored on the storage device 204 is indicated at block 214 and engages in database management and like functions related to data stored on the storage device 204. There may also be stored in the storage device 204 other software, such as one or more conventional operating systems, device drivers, communications software, etc. The historical claim transaction data 104 and the current claim transaction data 106, as previously described with reference to FIG. 1, are also shown in FIG. 2 as being stored on the storage device 204.

Figure 3:
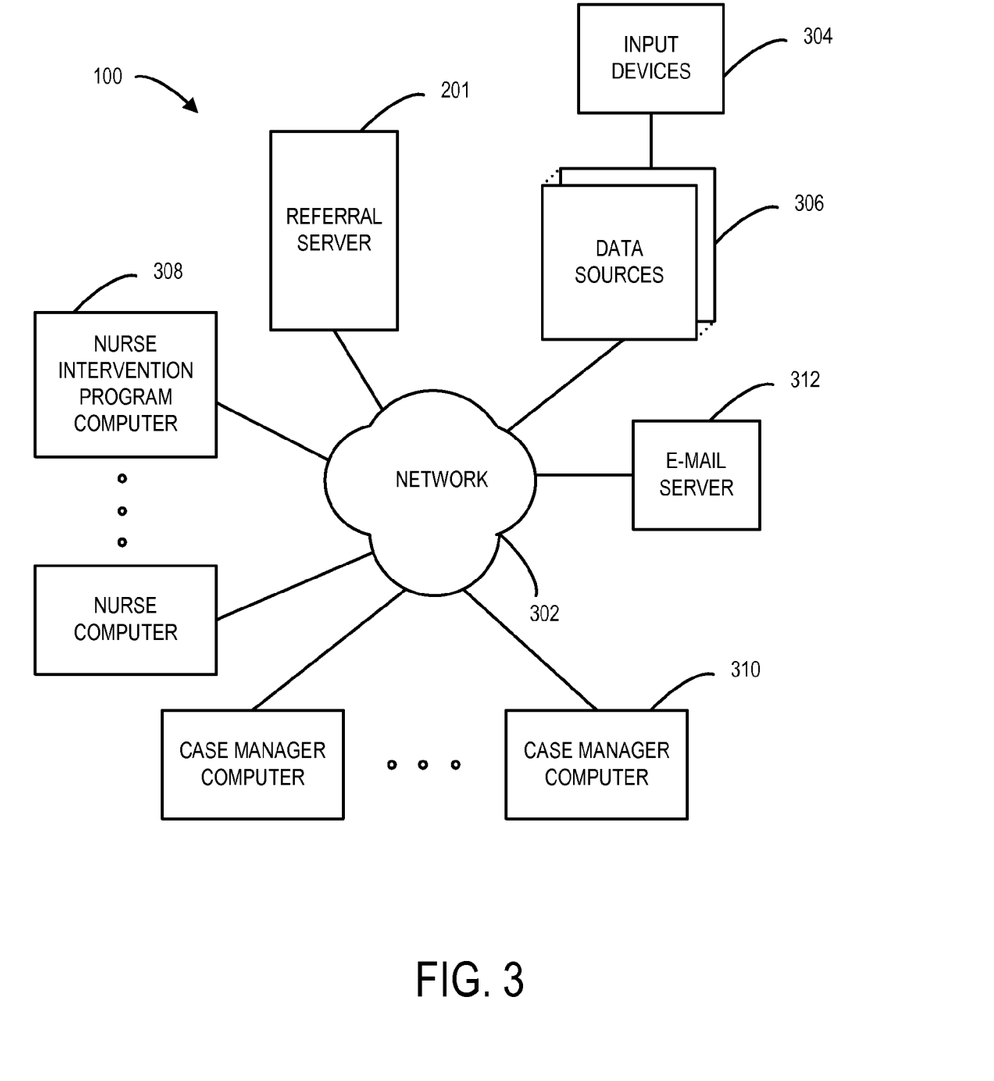
FIG. 3 is a block diagram that provides another representation of aspects of the system of FIG. 1.

FIG. 3 is another block diagram that presents the computer system 100 in a somewhat more expansive or comprehensive fashion (and/or in a more hardware-oriented fashion).

The computer system 100, as depicted in FIG. 3, includes the computer 201 of FIG. 2. The computer 201 is depicted as a "referral server" in FIG. 3, given that a function of the computer 201 is to selectively refer current claim transactions to a nurse intervention program of the insurance company. As seen from FIG. 3, the computer system 100 may further include a conventional data communication network 302 to which the computer/referral server 201 is coupled.

FIG. 3 also shows, as parts of computer system 100, data input device(s) 304 and data source(s) 306, the latter (and possibly also the former) being coupled to the data communication network 302. The data input device(s) 304 and the data source(s) 306 may collectively include the devices 108, 110 and 112 discussed above with reference to FIG. 1. More generally, the data input device(s) 304 and the data source(s) 306 may encompass any and all devices conventionally used, or hereafter proposed for use, in gathering, inputting, receiving and/or storing information for insurance company claim files.

Still further, FIG. 3 shows, as parts of the computer system 100, personal computers 308 assigned for use by nurses (who are members of the insurance company's nurse intervention program) and personal computers 310 assigned for use by case managers (who might also be members of or otherwise associated with the nurse intervention program). The personal computers 308, 310 are coupled to the data communication network 302.

Also included in the computer system 100, and coupled to the data communication network 302, is an electronic mail server computer 312. The electronic mail server computer 312 provides a capability for electronic mail messages to be exchanged among the other devices coupled to the data communication network 302. Thus the electronic mail server computer 312 may be part of an electronic mail system included in the computer system 100.

The computer system 100 may also be considered to include further personal computers (not shown), including, e.g., computers which are assigned to individual claim handlers or other employees of the insurance company.

Figure 4A:
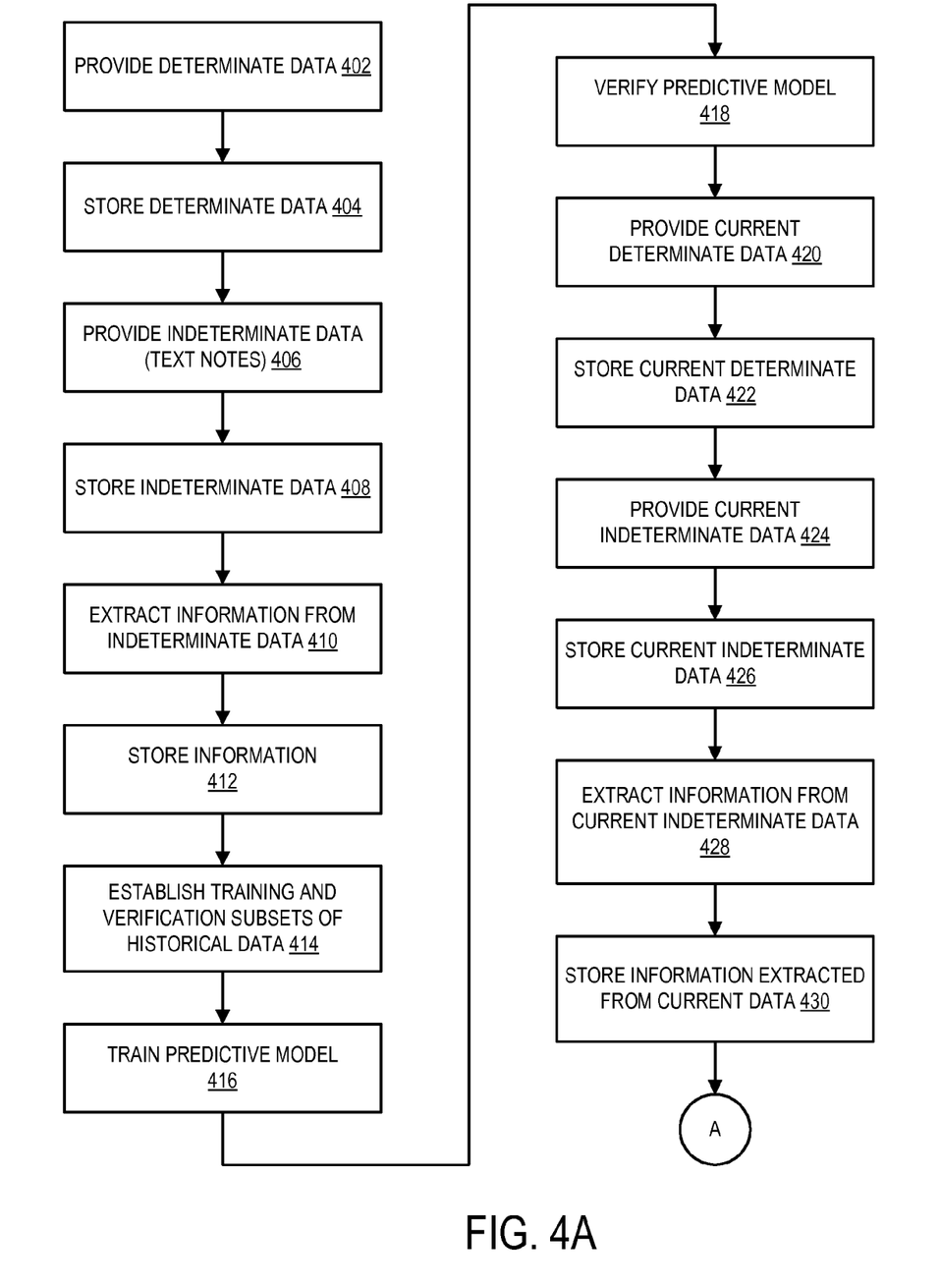
FIG. 4 is a flow chart that illustrates a process that may be performed in the computer system of FIGS. 1-3.

FIG. 4A is a flow chart that illustrates a process that may be performed in the computer system 100/computer 201 of FIGS. 1-3. At 402 in FIG. 4A, determinate data concerning historical claim transactions is provided to the computer system 100/computer 201. As indicated above, the determinate data may reflect the "hard facts" about the historical claim transactions. In addition, the determinate data may include, for each historical claim transaction, an indication as to whether or not the transaction in question benefited from a nurse intervention program. It will be understood that the historical claim transactions relate to claims made during a past period of time or periods of time. This information may, for example, be loaded into the computer 201 from a database and/or archive of claim files.

At 404, the determinate historical claim transaction data may be stored in the computer system 100/computer 201. At 406, indeterminate data for the historical claim transactions is provided to the computer system 100/computer 201. The indeterminate data may take the form, for example, of images of paper documents, digitized voice recordings, text files that reflect claim handlers' case file notes, or text files generated by OCR-processing paper documents or document images, or text files generated by speech-to-text conversion of digitized voice recordings. At 408, the indeterminate historical claim transaction data may be stored in the computer system 100/computer 201.

At 410 the computer system 100/computer 201 performs processing to extract significant information from the stored indeterminate historical claim transaction data. The extraction of information from the indeterminate historical claim transaction data may take one or more of a number of different forms. For example, the computer system 100/computer 201 may perform key word searches on text files included in the indeterminate historical claim transaction data. As still another example, names of entities (e.g., the treating physician's name) may be extracted from text files (e.g., claimant's attorney's demand package after OCR scanning) by entity analysis of the text files. One example of natural language processing may operate to mine claim handlers' opinions from the narrative text notes. At 412 in FIG. 4, the information extracted at 410 from the indeterminate historical claim transaction data is stored by the computer system 100/computer 201.

At 414, two mutually exclusive subsets of the historical claim transactions are formed. One of the two subsets is to be used for training the predictive model. The other of the two subsets is to be used for verifying the predictive model after it has been trained.

At 416, the predictive model is trained using the first one of the subsets of historical claim transaction data. In some embodiments, for example, the predictive model may be trained by using one or more types of regression analysis. In addition or alternatively, other types of pattern detection analysis may be applied to the first subset of historical claim transaction data. As another alternative, the predictive model may be implemented as a neural network. In some embodiments, the predictive model is of a kind that, for each claim transaction (after training) to which it is applied, the model generates a numerical output within a certain range. The output may be generated in such a manner that a higher output implies a higher likelihood that it would be worthwhile to refer the claim for nurse intervention.

After training of the predictive model, it is verified, as indicated at 418, by applying the model to the second subset of historical claim transaction data. The results of the verification processing are analyzed to confirm that the predictive model performs effectively in generally assigning higher outputs to the claim transactions in the second subset that actually benefited from the nurse intervention program.

At 420 in FIG. 4A, determinate data concerning current claim transactions is provided to the computer system 100/computer 201. Preferably the determinate data for the current claim transactions is of the same kinds as the determinate data for the historical claim transactions, as described above in connection with step 402. The determinate data may be loaded into the computer 201 from a database of current claim information. At 422, the determinate current claim transaction data may be stored in the computer system 100/computer 201.

At 424, indeterminate data for the current claim transactions is provided to the computer system 100/computer 201. Preferably the indeterminate data for the current claim transactions is of the same kinds as the indeterminate data for the historical claim transactions, as described above in connection with step 406. At 426, the indeterminate current claim transaction data may be stored in the computer system 100/computer 201.

At 428, the computer system 100/computer 201 performs processing to extract significant information from the stored indeterminate current claim transaction data. Preferably this is done in the same manner as the information extraction described above in connection with step 410. At 430, the information extracted at 428 from the indeterminate current claim transaction data is stored by the computer system 100/computer 201.

Figure 4B:
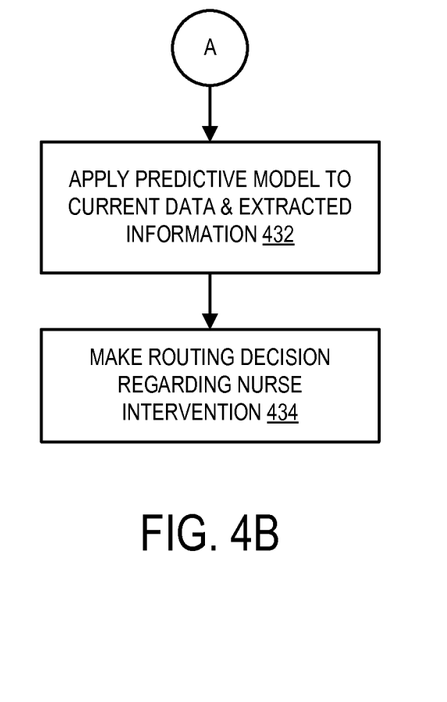

Referring now to FIG. 4B, at 432 the predictive model is applied to the determinate data, and to the information extracted at 428 from the indeterminate data, for one of the current claim transactions. (One could also say that the determinate data and the information extracted from the indeterminate data are applied to the predictive model.) The operation of the predictive model results in an output being generated for the current claim transaction in question. As indicated by previous discussion, the output is indicative of a determination by the predictive model as to the likelihood that the current claim would benefit from the nurse intervention program, with a higher output indicating a greater likelihood that the claim will benefit.

At 434 in FIG. 4, the computer 201 makes a routing decision with respect to the current claim transaction applied to the predictive model at 432. This decision is based on the output generated from the predictive model for the current claim transaction in question. From ensuing discussion, it will be understood that the routing decision may be whether to refer the current claim transaction in question to the insurance company's nurse intervention program.

Figure 5:
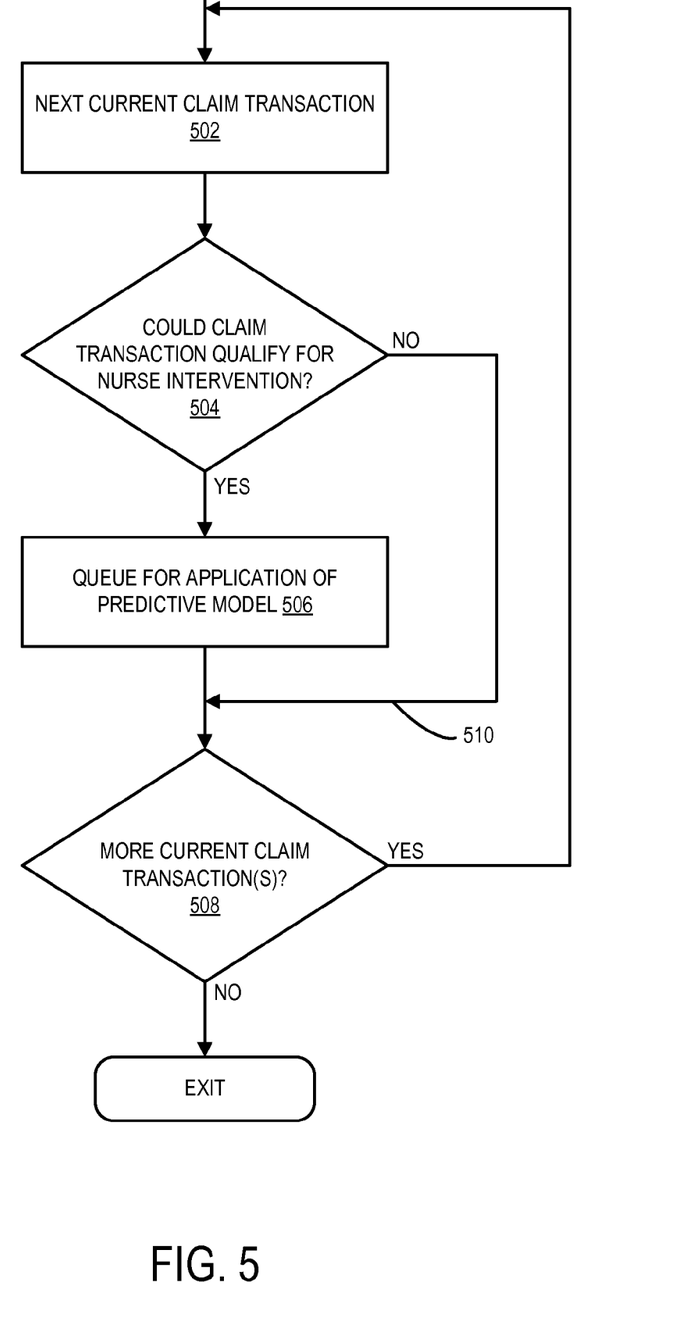
FIG. 5 is a flow chart that illustrates aspects of the process of FIGS. 4A and 4B according to some embodiments.
Figure 6:
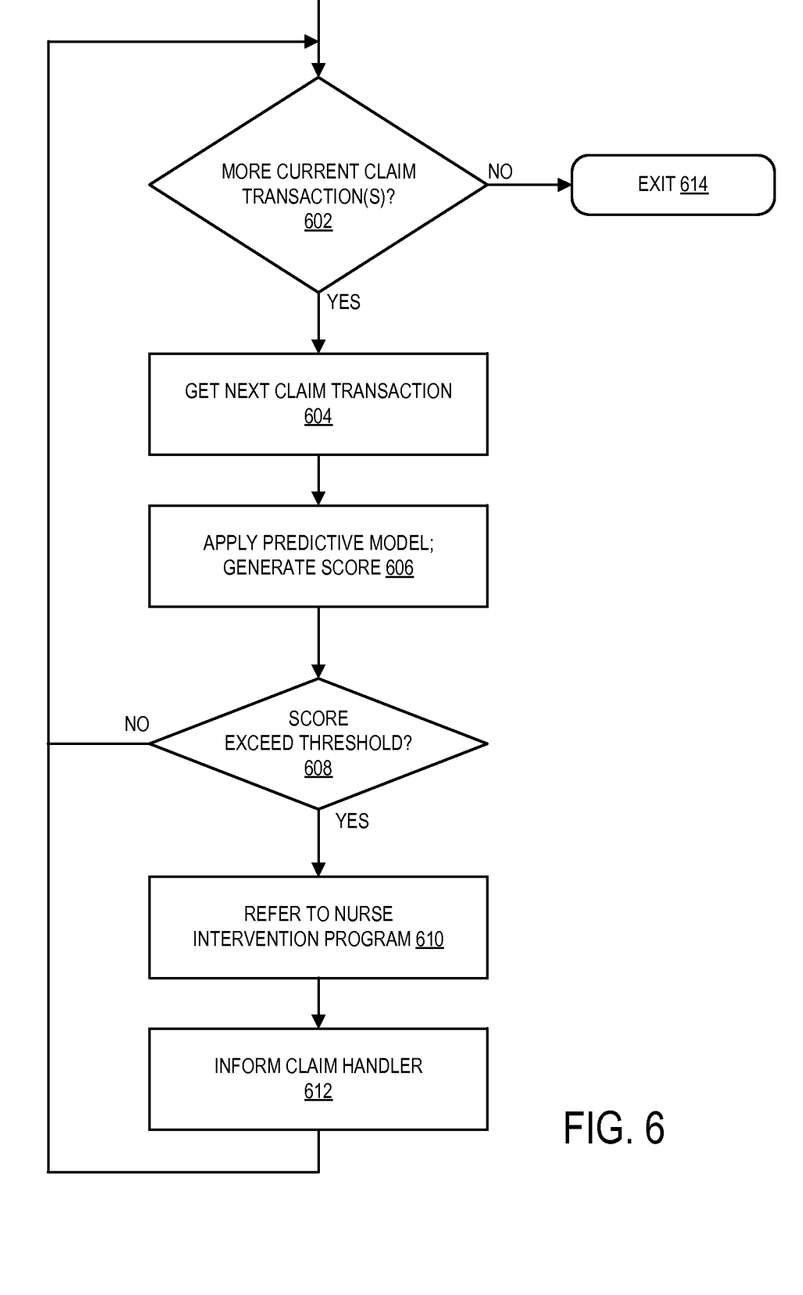
FIG. 6 is a flow chart that illustrates aspects of the process of FIGS. 4A and 4B in accordance with some embodiments.

FIGS. 5 and 6 are flow charts that illustrate additional details of the process of FIGS. 4A and 4B. Referring initially to FIG. 5, at 502 data for the next (or first) current claim transaction in a batch of transactions to be screened is accessed. Then, at decision block 504 the computer system 100/computer 201 determines whether the current claim transaction accessed at 502 qualifies for consideration for referral to a nurse intervention program. That is, certain current claim transactions may fall into categories such that the current claim transaction is not worth analyzing by the predictive model. Examples of current claim transactions that are will not benefit from nurse intervention may include, for example, worker's compensation claims arising from loss of life on the job or claims associated with an account (e.g., an employer) that does not provide such a benefit to employees. Thus it may be said that decision block 504 performs a "pre-screening" relative to the current claim transaction accessed at block 502.

If a determination is made at decision block 504 to the effect that it makes sense to apply the current claim transaction accessed at 502 to the predictive model, then block 506 may follow decision block 504. At block 506, the current claim transaction accessed at 502 is placed in a queue for application of the predictive model. Then decision block 508 follows block 506. At decision block 508, it is determined whether any more current claim transactions are awaiting analysis by the predictive model. If so, then the process of FIG. 5 loops back to block 502, and the next current claim transaction awaiting screening is accessed and subjected to "pre-screening" at decision block 504. However, if at decision block 508 it is determined that no further current claim transactions are awaiting analysis by the predictive model, then the process of FIG. 5 ends.

Considering again decision block 504, if a determination is made at that point that the current claim transaction accessed at block 502 is of a kind such that it does not make sense to apply the predictive model, then, per branch 510, the process of FIG. 5 skips from decision block 504 to decision block 508, omitting block 506 with respect to the current claim transaction accessed at block 502.

Thus, in such cases, the current claim transaction accessed at block 502 is not queued for application of the predictive model and is not screened for possible referral to the nurse intervention program.

Referring now to FIG. 6, the process illustrated therein begins with decision block 602. At decision block 602 the computer system 100/computer 201 determines whether there are any current claim transactions in the queue referred to in connection with block 506 of FIG. 5. If there is at least one current claim transaction in the queue, then block 604 follows decision block 602. At 604, the computer system 100/computer 201 accesses the next current claim transaction in the queue. Then, at 606, the computer system 100/computer 201 applies the predictive model to the current claim transaction accessed at 604. From previous discussion it will be recognized that the application of the predictive model to the current claim transaction in question results in the computer system 100/computer 201 generating an output for the current claim transaction in question, where the output is indicative of whether it is advisable that the current claim transaction in question should be referred to a nurse intervention program.

Decision block 608 follows block 606. At decision block 608, the computer system 100/computer 201 determines whether the output generated at 606 exceeds a predetermined threshold. The threshold may, for example, have been set at the time that the training of the predictive model was verified (block 418, FIG. 4A). The threshold may have been set in such a manner as to balance the potentially conflicting goals of avoiding false positive indications, while avoiding false negative determinations. The achievement of this balance may reflect the respective levels of outputs generated by the predictive model during verification processing to proper and improper historical claim transactions. According to other embodiments, the output of the predictive model is simply a "true/false" flag indicating whether or not the nurse intervention program is appropriate.

If it is determined at decision block 608 that the output generated at 606 exceeds the threshold, then block 610 follows decision block 608. At block 610, the computer system 100/computer 201 may refer the current claim transaction in question to a case manager and/or nurse associated with the nurse intervention program. This may be done by the computer system 100/computer 201 automatically e-mailing the electronic case file for the claim transaction to a manager. If more than one case manager or nurse is available to receive the referral of the claim transaction, then the computer system 100/computer 201 may automatically select the party who is to receive the referral based on one or more factors such as the type of claim, the nurse's qualifications and/or experience, the case manager's current workload, etc.

In some embodiments, the computer system 100/computer 201 may cause the claim transactions referred to each case manager or nurse, and/or to the nurse intervention program as a whole, to be queued according to the outputs generated for the claim transactions. That is, claim transactions having higher outputs assigned by the predictive model may be placed higher in the individual case manager or nurse queues and/or in the overall nurse intervention program's queue.

Block 612 may follow block 610. At block 612 the computer system 100/computer 201 automatically notifies the claim handler to whom the claim transaction had been assigned that the claim transaction was being referred to the nurse intervention program. At the same time, the computer system 100/computer 201 may inform other interested branches of the insurance company that the claim transaction is being referred to the nurse intervention program.

After block 612, the process of FIG. 6 loops back to decision block 602 to determine whether there are other claim transactions in the queue to be analyzed by the predictive model. If, at a point when decision block 602 is reached, there are no more claim transactions in the queue, then the process of FIG. 6 ends, as indicated at branch 614.

Figure 7:
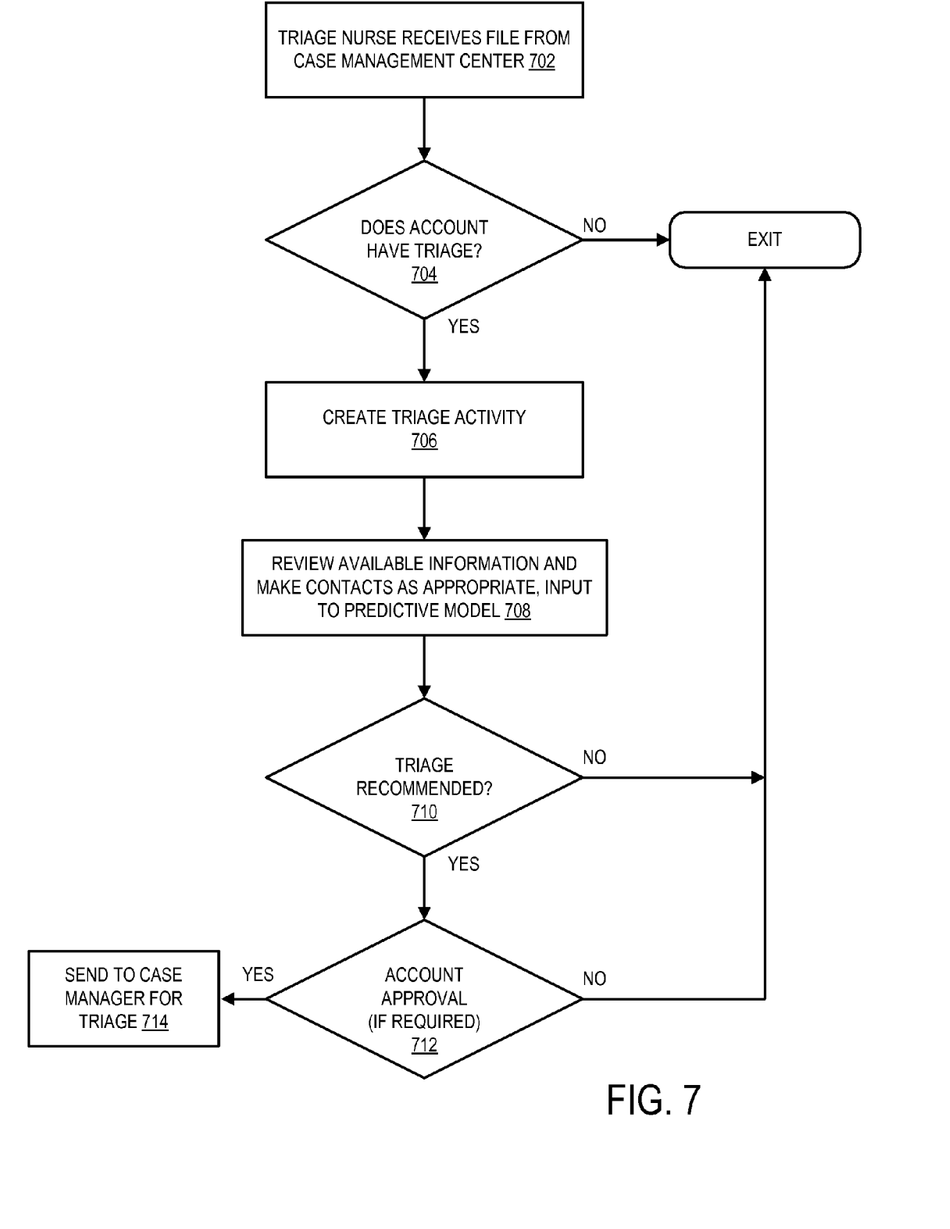
FIG. 7 is a flow chart illustrating a case management process for a nurse intervention program.

FIG. 7 is a flow chart illustrating a case management process for a nurse intervention program. At 702, a triage nurse may receive a file from a case manager and/or case management center. The file might comprise, for example, an electronic file, workbasket, and/or task list generated in response to a notice of injury (e.g., a first notice of injury) associated with a worker's compensation claim or a bodily injury claim.

At 704, it is determined whether or not the account associated with the file provides triage as a potential benefit for employees. If not, the process simply ends.

The determination might be based on, for example, Special Account Instructions (SAI) associated with an employer, union, or other provider of benefits.

If the account does provide triage as a potential benefit for employees, a triage activity may be created at 706. The triage activity might be associated with, for example, an electronic, automated insurance processing workflow system.

The available information may be reviewed at 708 and contacts may be made as appropriate to determine additional information. For example, a doctor, employer, and/or injured worker might be contacted to determine additional details associated with an injury or accident. The additional information might be entered, for example, by a telephonic triage case manager.

At 708, the available information may also be provided to a predictive model as described herein. Note that the predictive model might use any of a number of different parameters (associated with historical cases or the case currently being reviewed) to determine if a nurse intervention program should be utilized based on a predicted ultimate medical claim severity and/or a predicted ultimate indemnity claim severity.

For example, the decision might be at least partially based on information extracted from narrative text notes (e.g., medical notes) indicating a prior injury, alcohol related co-morbidity information, drug related co-morbidity information, tobacco related co-morbidity information, arthritis related co-morbidity information, diabetes related co-morbidity information, and/or obesity related co-morbidity information. Other types of information that might be utilized include demographic information (e.g., the age of a worker), injury details, accident information, employment information, and/or financial information (e.g., a worker's salary). Still other examples of information might include a Part Of Body (POB) injured, a Nature Of Injury (NOI), an industry or occupation, a medical paid or reserves amount, an indemnity paid or reserves amount, a previously noted injury, a presence of a co-morbidity, and/or a claim complexity. According to some embodiments, a predictive model may utilize an injury matrix to determine whether or not nurse intervention is appropriate. For example, different classes of injuries might be assigned different scores or weights when scoring an injury.

If triage is not recommended at 710, the process ends. If triage is recommended, it is determined whether the account associated with the file needs to approve triage before it is provided to a claimant. If approval is required and the account declines to approve the file at 712, the process ends. If the account does approve triage (or if the account does not require pre-approval), the file may sent to the case manager for triage at 714.

Note that the processes described herein might be performed more than once for a particular injury or claim. For example, the process of FIG. 7 could first be performed within three days of an injury and the be re-performed again after another period of time (e.g., twenty five days after the injury).

In some embodiments, the nurse intervention program may receive referrals via other channels than referral based on a predictive model. For example, referrals may also be from claim handlers, or from outside sources, directly from insurance agents, etc. Other referrals for the nurse intervention may take place selectively/pro-actively based on other sources when appropriate claim transactions are identified. Moreover, in some embodiments, some or all of the above-mentioned communications among case managers, claim handlers, and nurses may be via an automated messaging system, such as the electronic mail system referred to above in conjunction with FIG. 3.

Figure 8:
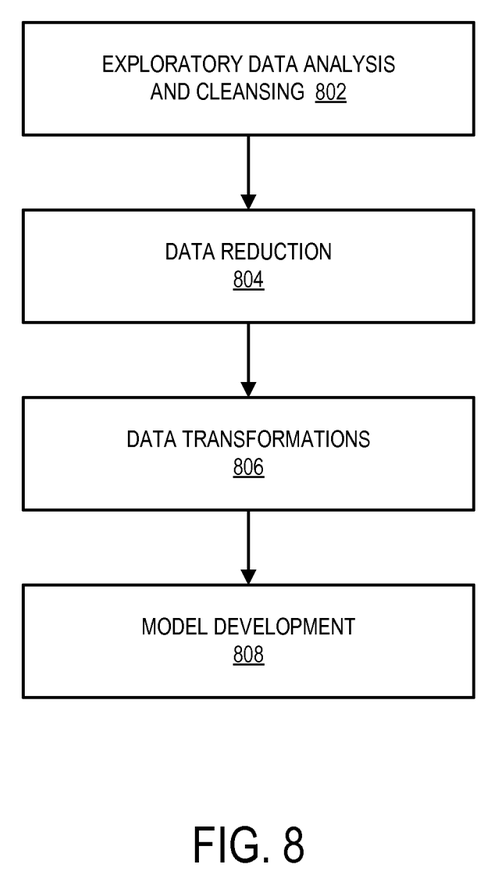
FIG. 8 is a flow chart illustrating how a predictive model might be trained according to some embodiments.

According to some embodiments, a predictive model is used to facilitate a provisioning of nurse intervention services. Note that the predictive model might be designed and/or trained in a number of different ways. For example, FIG. 8 is a flow chart illustrating how a predictive model might be created according to some embodiments. At 802, data to be input to the predictive model may be analyzed, scrubbed, and/or cleaned. This process might involve a broad review of the relevant variables that may be included in the sample data. Variables might be examined for the presence of erroneous values, such as incorrect data types or values that don't make sense. Observations with such "noisy" data or missing data may be removed from the sample. Similarly, any data points that represent outliers are also managed.

At 804, a data reduction process might be performed. This might occur, for example, between variables in the data sample and/or within specific variables. According to some embodiments, certain variables may be associated with one another and the number of these variables may be reduced. For example, it might be noted that injuries to the left shoulder generally have values similar to injuries to the right shoulder. Within certain variables, the raw values may represent a level of information that is too granular. These raw values might then be categorized to reduce the granularity. A goal of the data reduction process may be to reduce the dimensionality of the data by extracting factors or clusters that may account for the variability in the data.

At 806, any necessary data transformations may be performed. Transformations of dependent and/or independent variables in statistical models can be useful for improving interpretability, model fit, and/or adherence to modeling assumptions. Some common methods may include normalizations of variables to reduce the potential effects of scale and dummy coding or other numeric transformations of character variables.

Once these steps are complete, the predictive model may be developed at 808. Depending on the nature of the desired prediction, various modeling techniques may be utilized and compared. The list of independent variables may be narrowed down using statistical methods as well as business judgment. Lastly, the model coefficients and/or weights may be calculated and the model algorithm may be completed. For example, it might be determined that injuries to a knee are generally twice as serious as injuries to a shoulder (and thus, according to some embodiments, a knee injury might be weighted more as compared to a shoulder injury).

Figure 9:
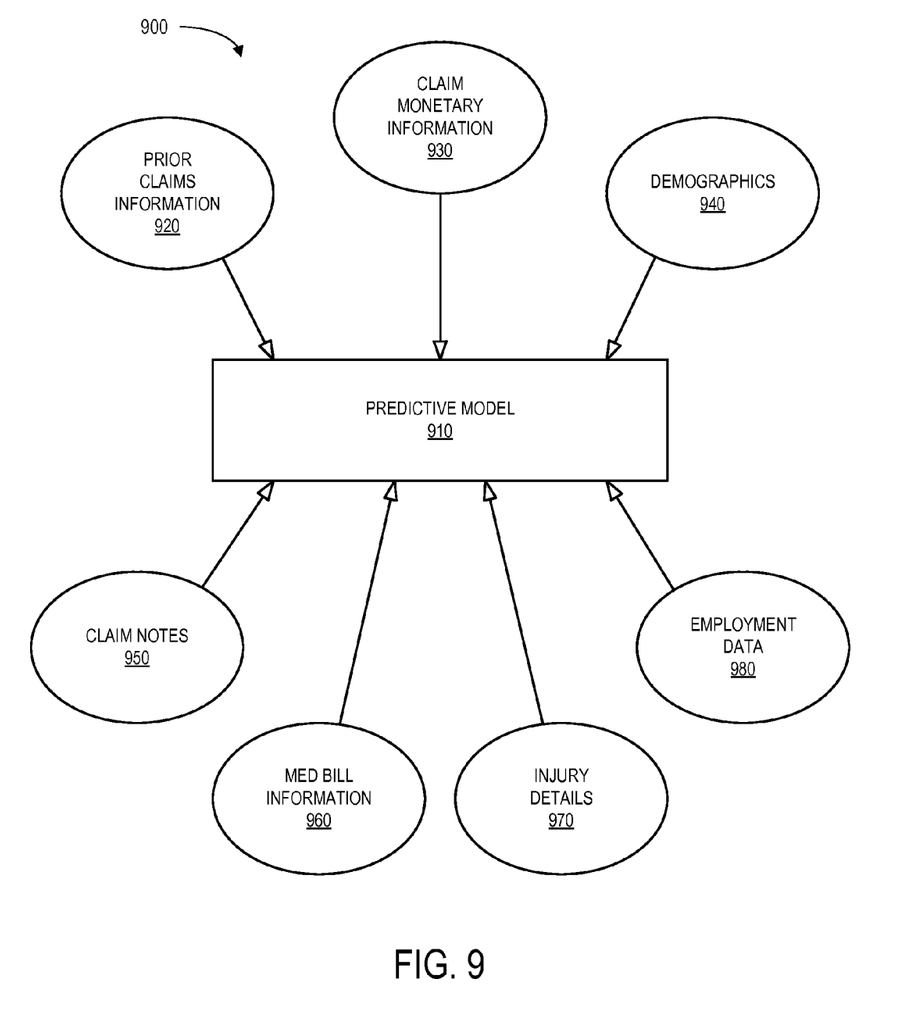
FIG. 9 illustrates predictive model inputs according to some embodiments.

Note that many different types of data might be used to create, evaluate, and/or use a predictive model. For example, FIG. 9 is a block diagram of a system 900 illustrating inputs to a predictive model 910 according to some embodiments. In this example, the predictive model 910 might receive information about prior claims 920 (e.g., historical data about prior workers compensation claims). Moreover, the predictive model 910 might receive monetary information about claims 930 (e.g., a total amount of payments made in connection with a claim) and/or demographic information 940 (e.g., the age or sex of a claimant). According to some embodiments, claim notes 950 are input to the predictive model 910 (e.g., an keywords may be extracted from the notes 950). Other types of information that might be provided to the predictive model 910 include medical bill information 960 (e.g., including information about medical care that was provided to a claimant), injury details 970 (e.g., which part or parts of the body have been injured), and employment data 980 (e.g., an employee's salary or how long an employee has worked for an employer).

Figure 10:
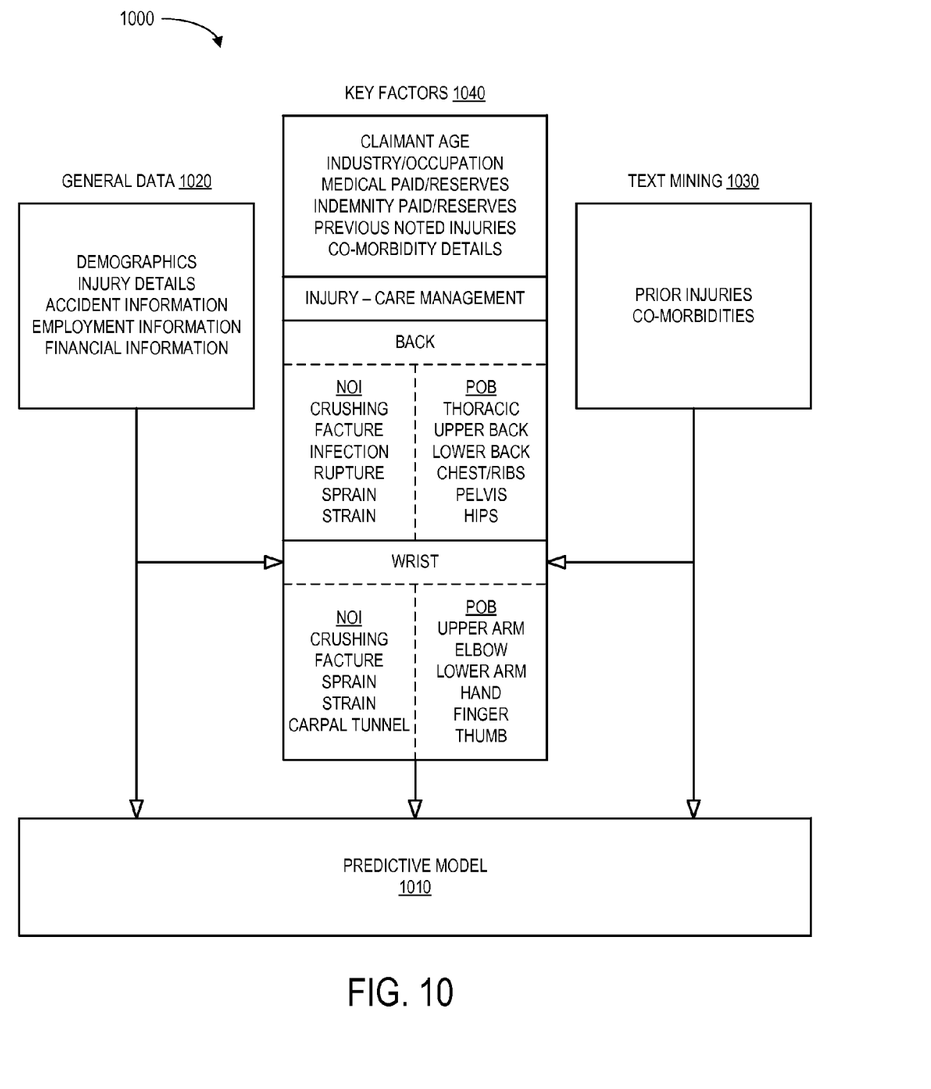
FIG. 10 is a more detailed example of particular types of predictive model inputs in accordance with some embodiments.

FIG. 10 is a more detailed system 1000 illustrating in more detail particular types of inputs that might be provided to a predictive model 1010 in accordance with some embodiments. For example, the predictive model 1010 might receive, in connection with historical and/or current claim transaction, general data 1020 such as demographic information, injury details, accident information, employment information, and/or financial information. The predictive model 1010 may also receive information found via text mining 1030, such as information about prior injuries and/or co-morbidity information associated with a claimant.

Some of the general data 1020 and information determined via text mining 1030 may be considered, stored, and/or further processed as "key factors" 1040 (e.g., factors that might be of particular relevance when determining whether or not utilization of a nurse intervention program is appropriate for a particular claim). For example, a claimant age, an industry or occupation associated with a claim, an amount of indemnity paid (and/or an amount of reserves), previously noted injuries, and/or co-morbidity information might be especially important when determining whether or not to provide nurse intervention program services for a claim.

One type of data that may be of particular relevance is injury information associated with an amount and type of care management that might be provided for a claimant. According to some embodiments, the injury information be structured as a matrix or template of potential injuries (e.g., and in some embodiments, various elements of the data structure may be provided with appropriate weighing factors as described with respect to FIG. 8). For example, as illustrated in FIG. 10, key factors 1040 for a "back" injury might include Nature of Injury (NOI) information (e.g., crushing, fracture, or infection) and Part of Body (POB) information (e.g., thoracic, upper back, or lower back). Similar information may be provided for other types of injuries (e.g., wrist, eye, or lung). The general data 1020, text mining information 1030, and key factors 1040 might then be used by the predictive model 1010 for training and/or current claim evaluations.

The process descriptions and flow charts contained herein should not be considered to imply a fixed order for performing process steps. Rather, process steps may be performed in any order that is practicable.

The present invention has been described in terms of several embodiments solely for the purpose of illustration. Persons skilled in the art will recognize from this description that the invention is not limited to the embodiments described, but may be practiced with modifications and alterations limited only by the spirit and scope of the appended claims.

What is claimed is:

1. A computer system for facilitating provisioning of a nurse intervention program, comprising:
    a data storage module for receiving, storing, and providing access to data related to historical insurance claim information, including historical injury information and historical insurance claim result information, and to current insurance claim transactions, including current insurance claim transaction injury information;
    a predictive model component, coupled to the data storage module, for determining whether to identify one of said current insurance claim transactions for referral to the nurse intervention program;
    a computer processor for executing programmed instructions and for storing and retrieving said data related to current insurance claim transactions;
    a program memory, coupled to the computer processor, for storing program instruction steps for execution by the computer processor;
    a model training component, coupled to the computer processor, for (i) automatically training the predictive model component based on a first subset of the data related to the historical insurance claim information, including both historical injury information and historical insurance claim result information and (ii) automatically verifying the trained predictive model component based on a second subset of the data related to the historical insurance claim information, different than the first subset, in accordance with program instructions stored in the program memory and executed by the computer processor, thereby providing a trained and verified predictive model component;
    an output device, coupled to the computer processor, for outputting an output indicative of whether said one of said current insurance claim transactions should be referred to the nurse intervention program, wherein the computer processor generates the output in accordance with program instructions in the program memory and executed by the computer processor, said output generated in response to a notice of injury received in connection with said one of said current insurance claim transaction and being based on an application of data for said one of said current insurance claim transactions to the trained and verified predictive model component; and
    a routing module for directing workflow based on the output from the output device.

2. The computer system of claim 1, wherein different current insurance claim transactions are associated with different accounts, and said generation of said output is further based on the account associated with the current insurance claim transaction.

3. The computer system of claim 1, wherein the data stored in the data storage module includes both determinate and indeterminate data.

4. The computer system of claim 3, wherein the indeterminate data includes narrative text notes.

5. The computer system of claim 4, wherein the narrative text notes are associated with at least one of: (i) a prior injury, or (ii) co-morbidity information.

6. The computer system of claim 5, wherein the narrative text notes are associated with at least one of: (i) alcohol related co-morbidity information, (ii) drug related co-morbidity information, (iii) tobacco related co-morbidity information, (iv) arthritis related co-morbidity information, (v) diabetes related co-morbidity information, or (vi) obesity related co-morbidity information.

7. The computer system of claim 1, wherein the routing module routes said one of the current insurance claim transactions to the nurse intervention program based on the output from the output device.

8. The computer system of claim 1, wherein the routing module routes the current insurance claim transaction to a case management center associated with the nurse intervention program.

9. The computer system of claim 1, wherein the insurance claim transactions are worker's compensation claims.

10. The computer system of claim 1, wherein the insurance claim transactions are bodily injury claims.

11. The computer system of claim 1, wherein said generation of said output is performed after a first time period based on a predicted ultimate insurance claim severity and is re-performed after a second time period based on a re-predicted ultimate insurance claim severity, the second time period being different than the first time period.

12. The computer system of claim 1, wherein said generation of said output is based on at least one of: (i) demographic information, (ii) injury details, (iii) accident information, (iv) employment information, or (v) financial information.

13. The computer system of claim 1, wherein said generation of said output is based on at least one of: (i) a part of body injured, (ii) a nature of injury, (iii) a claimant age, (iv) an industry or occupation, (v) a medical paid or reserves amount, (vi) an indemnity paid or reserves amount, (vii) a previously noted injury, (viii) a presence of a co-morbidity, (ix) a claim complexity, (x) an injury matrix, or (xi) a key factor.

14. A computer-implemented method of managing nurse intervention program decisions, the method comprising:
    storing, in a computer storage unit, historical claim data, including historical injury information and historical insurance claim result information;
    using a first subset of the historical claim data, by a computer processor, to develop a predictive model having a plurality of historical claim data inputs and variables, developing the predictive model including:
        performing data cleansing to eliminate one or more data inputs in the predictive model;
        performing data reduction to reduce the number of variables in the predictive model; and
        performing data transformations to normalize variables in the predictive model,
    the predictive model for evaluating claim transactions to determine whether to refer the claim transactions to a nurse intervention program;
    using a second subset of the historical claim data, different than the first subset, to verify the developed predictive model;
    automatically applying, by the computer processor, the verified predictive model to the data for the current claim transactions to generate a respective output for each of the current claim transactions, said generation being automatically performed for a current insurance claim both after a first time period and a second time period, the second time period being different than the first time period; and
    selectively routing, by the computer processor, ones of the current claim transactions to a case management center associated with the nurse intervention program based on the outputs generated by the predictive model.

\* \* \* \* \*